United States Patent
Rumsey

(10) Patent No.: US 8,568,307 B2
(45) Date of Patent: Oct. 29, 2013

(54) HANDS FREE USE OF A BALFOUR BLADE

(75) Inventor: Todd Rumsey, Fort Wayne, IN (US)

(73) Assignee: Tippmann Medical, LLC, Fort Wayne, IN (US)

( * ) Notice: Subject to any disclaimer, the term of this patent is extended or adjusted under 35 U.S.C. 154(b) by 686 days.

(21) Appl. No.: 12/813,960

(22) Filed: Jun. 11, 2010

(65) Prior Publication Data

US 2010/0317927 A1    Dec. 16, 2010

Related U.S. Application Data

(60) Provisional application No. 61/186,043, filed on Jun. 11, 2009.

(51) Int. Cl.
*A61B 1/32* (2006.01)

(52) U.S. Cl.
USPC .......................................... 600/226; 600/215

(58) Field of Classification Search
USPC ........................ 600/201, 210, 215, 216–228
See application file for complete search history.

(56) References Cited

U.S. PATENT DOCUMENTS

| | | | |
|---|---|---|---|
| 1,708,578 A | 4/1929 | Hyde | |
| 2,693,795 A * | 11/1954 | Grieshaber | 600/213 |
| 3,542,015 A | 11/1970 | Steinman | |
| 4,151,838 A | 5/1979 | Crew | |
| 4,239,036 A | 12/1980 | Krieger | |
| 4,344,420 A * | 8/1982 | Forder | 600/232 |
| 4,380,999 A | 4/1983 | Healy | |
| D314,825 S | 2/1991 | Torre | |
| 5,065,739 A * | 11/1991 | Forrest et al. | 600/230 |
| 5,307,805 A | 5/1994 | Byrne | |
| 5,514,076 A | 5/1996 | Ley | |
| 5,899,853 A | 5/1999 | Fowler, Jr. | |
| 5,964,697 A | 10/1999 | Fowler, Jr. | |
| 5,964,698 A | 10/1999 | Fowler | |
| 6,834,837 B2 * | 12/2004 | Schilt et al. | 248/284.1 |
| 2008/0076968 A1 * | 3/2008 | Bollier et al. | 600/227 |

FOREIGN PATENT DOCUMENTS

| | | | |
|---|---|---|---|
| FR | 2 570 266 A1 | 3/1986 | |
| FR | 2737102 A1 * | 1/1997 | |

* cited by examiner

*Primary Examiner* — Nicholas Woodall
*Assistant Examiner* — Larry E Waggle, Jr.
(74) *Attorney, Agent, or Firm* — Birch, Stewart, Kolasch & Birch, LLP

(57) ABSTRACT

A self retaining adaptor enables hands free use of a balfour retractor blade. An elongated element includes a proximal end and a distal end. The elongated element includes an intermediate portion extending from the proximal end to the distal end. The intermediate portion has a predetermined width with an elongated slot being formed therein. The elongated slot includes a predetermined number of enlarged openings formed at predetermined intervals along the length of the slot. The enlarged openings enable the insertion of a wing-nut connection for attaching a member to the elongated element.

20 Claims, 5 Drawing Sheets

HANDS FREE USE OF A BALFOUR BLADE

CROSS-REFERENCE TO RELATED APPLICATIONS

The present application claims priority under 35 USC 119 to Provisional Patent Application No. 61/186,043 filed on Jun. 11, 2009 the entire contents of which are hereby incorporated by reference.

BACKGROUND OF THE INVENTION

1. Field of the Invention

The present invention relates to a device for allowing the hands free use of a balfour retractor blade in operative procedures requiring exposure of the lower pelvis.

2. Description of Background Art

Heretofore the use of a balfour retractor blade in operative procedures requiring exposure of the lower pelvis, in particular performing a C-section on a pregnant woman, required the use of one or two hands. This presents an inconvenience to a physician who may be required to perform an additional procedure while using the balfour blade.

A retractor is used as a surgical instrument for a surgeon to either actively separate the edges of a surgical incision or wound or to hold back underlying organs and tissues, so that body parts under the incision may be accessed. Retractors are available in many shapes, sizes and styles. A retractor is usually a simple handheld steel tool possessing a curved, hooked or angled blade fitted with a handle. When the retractor is in place, the retractor maintains the desired position of a given organ or region of tissue. Retractors may be handheld, clamped in situ, or suspended at the end of a robotic arm. A retractor normally requires the use of at least one hand to hold the retractor in place during use.

In addition, the lower pelvic region is a difficult area of the abdomen to expose for surgery. The lower pelvic region is confined by the thick pelvic bones which establish an anatomical limit to the size of the operating field no matter how large an incision is made. In addition, the loops of intestine which normally occupy this area interfere with the surgeon and must be kept away from the operating field during the entire course of the operation. In view of the confined area and the tendency of the intestine to seek their natural resting place, a retractor is used for surgery in the pelvic region.

Prior retractors used in this type of surgery for maintaining the wound in an open position require the use of at least one of the surgeon's hands. This is necessary to hold the intestines out of the operating field when the surgeon is performing a C-section and is required to maintain the large colon, gallbladder, etc. in an area away from the delivery of the baby. On some occasions, it has become standard practice to supplement the use of standard retractors by using surgical assistants to hold the intestines out of the field by hand.

SUMMARY AND OBJECTS OF THE INVENTION

It is an object of an embodiment of the present invention to provide a device for enabling hands free use of a balfour retractor blade. An elongated element is provided having a proximal end and a distal end. The elongated element includes an intermediate portion extending from the proximal end to the distal end. The intermediate portion includes a predetermined width with an elongated slot being formed therein. A self retaining adaptor includes a free end and a secured end. The secured end includes a projection extending therefrom for positioning within the elongated slot in the intermediate portion. A retaining member is operatively attached to the projection for mounting the secured end of the self retaining adaptor in a fixed position relative to the intermediate portion. A predetermined weight may be attached to the free end of the self retaining adaptor for enabling hands free use of the balfour retractor blade.

According to an embodiment of the present invention, the elongated slot extends from adjacent the proximal end of the elongated element to a predetermined point adjacent to the distal end of the elongated element. The elongated slot includes at least one enlarged portion for receiving the retaining member through the enlarged portion for enabling a positioning of the self retaining retractor relative to the elongated slot.

According to an embodiment of the present invention, the retaining member includes a wing nut and the projection is threaded for enabling the self retaining adaptor to be secured relative to the elongated slot in the elongated element by threading the wing nut on the threaded projection for securing the self retaining adaptor relative to the elongated element.

According to an embodiment of the present invention, the secured end of the self retaining adaptor includes a proximal end and a distal end. The proximal end includes the projection extending therefrom. The free end includes a proximal end and a distal end. The proximal end of the free end is pivotably mounted relative to the distal end of the secured end.

According to an embodiment of the present invention, a ratchet connection is formed adjacent to the pivotable connection of the proximal end of the free end and the distal end of the secured end for holding the positioning of the free end relative to the secured end in a plurality of angular relationships relative to each other.

According to an embodiment of the present invention, the distal end of the free end includes an aperture formed therein for mounting a predetermined weight to enabling the hands free use of the balfour retractor blade.

According to an embodiment of the present invention, the distal end of the free end includes an aperture formed therein for mating with an attaching mechanism for securing a cord to the distal end of the free end for securing a predetermined weight to the cord for enabling the hands free use of the balfour retractor blade.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Figure 1:
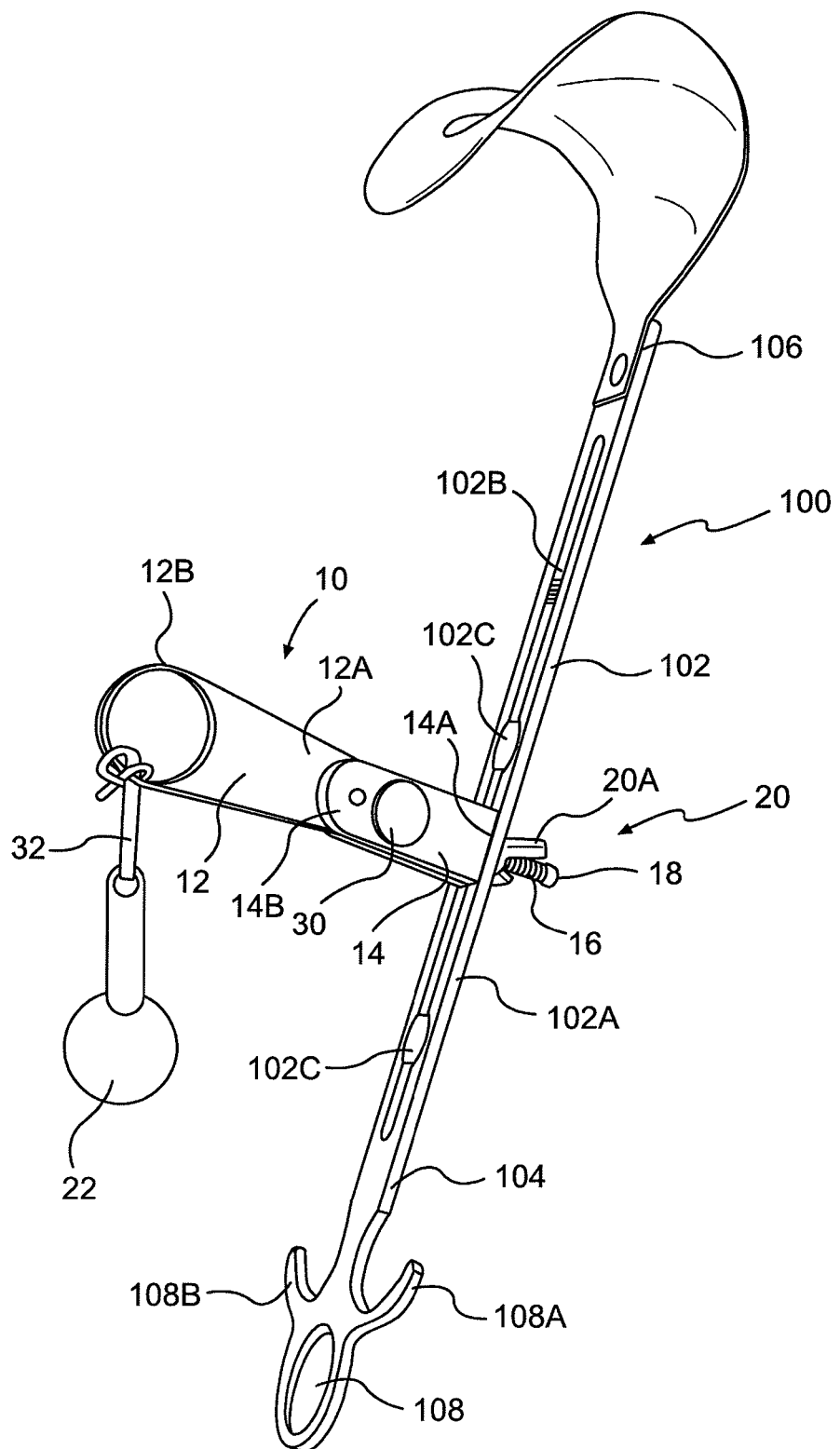
FIG. 1 is a perspective view of a balfour retractor blade with a self retaining adaptor extending substantially orthogonally therefrom.

As illustrated in FIGS. 1-4, an embodiment of the present invention provides a self retaining adaptor 10 for enabling hands free use of a balfour retractor blade 100. An elongated element 102 includes a proximal end 104 and a distal end 106. The elongated element 102 includes an intermediate portion 102A extending from the proximal end 104 to the distal end 106. The intermediate portion 102A has a predetermined width with an elongated slot 102B being formed therein. The slot 102B includes a predetermined number of enlarged openings 102C formed at predetermined intervals along the length of the slot 102B. The enlarged openings 102C enable the insertion of a wing-nut connection for attaching a member to the elongated element 102.

The proximal end 104 of the balfour retractor blade 100 includes an aperture 108 with finger engaging projections 108A and 108B. The distal end 106 of the balfour retractor blade 100 includes a curved blade 110 for ensuring the proper positioning of the internal organs of a patient to keep the internal organs such as the intestines, gallbladder, etc. out of the operating area when the surgeon is performing a C-section.

A self retaining adaptor 10 includes a free end 12 and a secured end 14. The secured end 14 includes a projection 16 extending therefrom for positioning within the elongated slot 102B in the intermediate portion 102A.

A retaining member 20 is operatively attached to the projection for mounting the secured end 14 of the self retaining adaptor 10 in a fixed position relative to the intermediate portion 102A.

Figure 2:
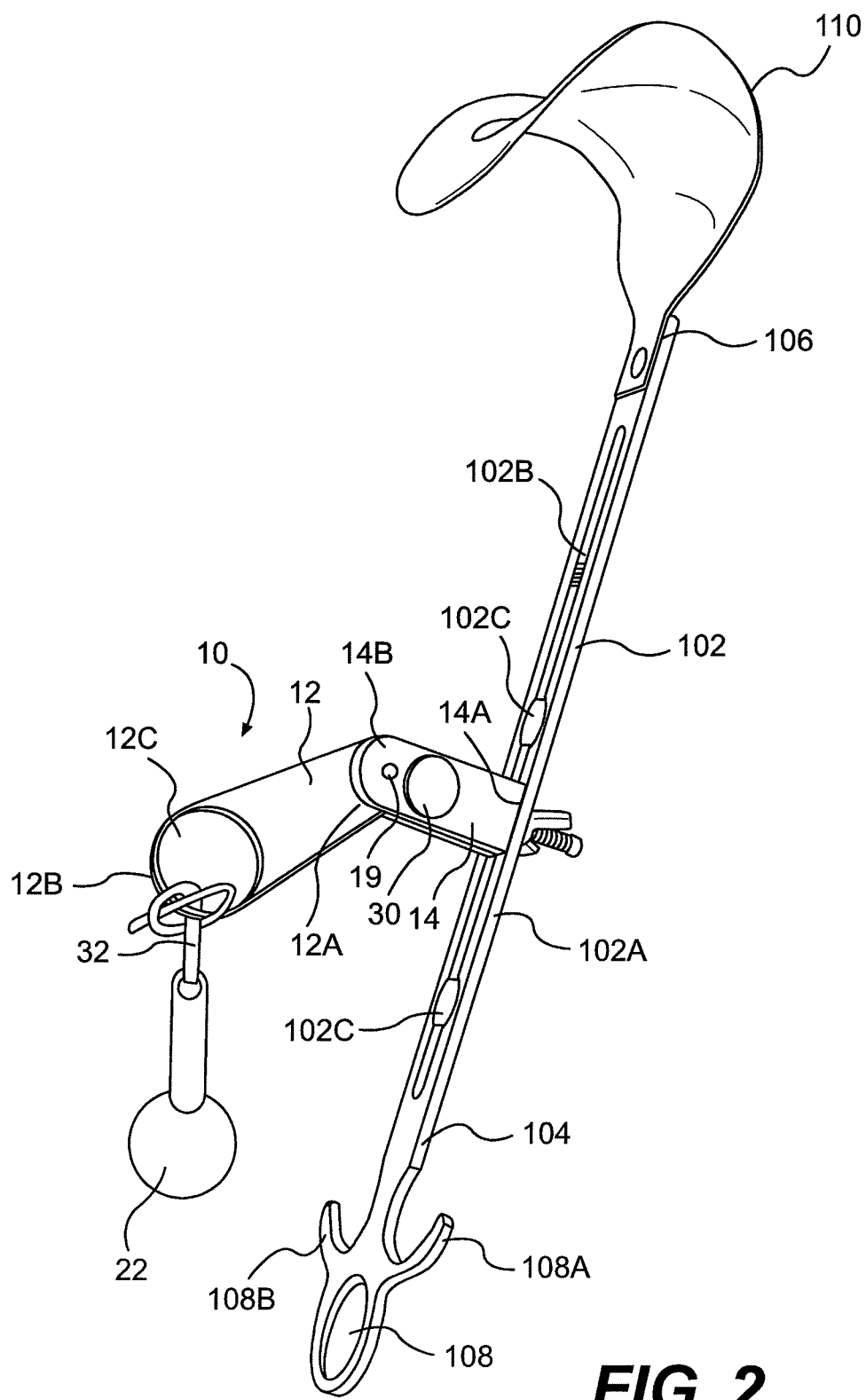
FIG. 2 is a perspective view of a balfour retractor blade with the self retaining adaptor extending at a predetermined angle therefrom.
Figure 3:
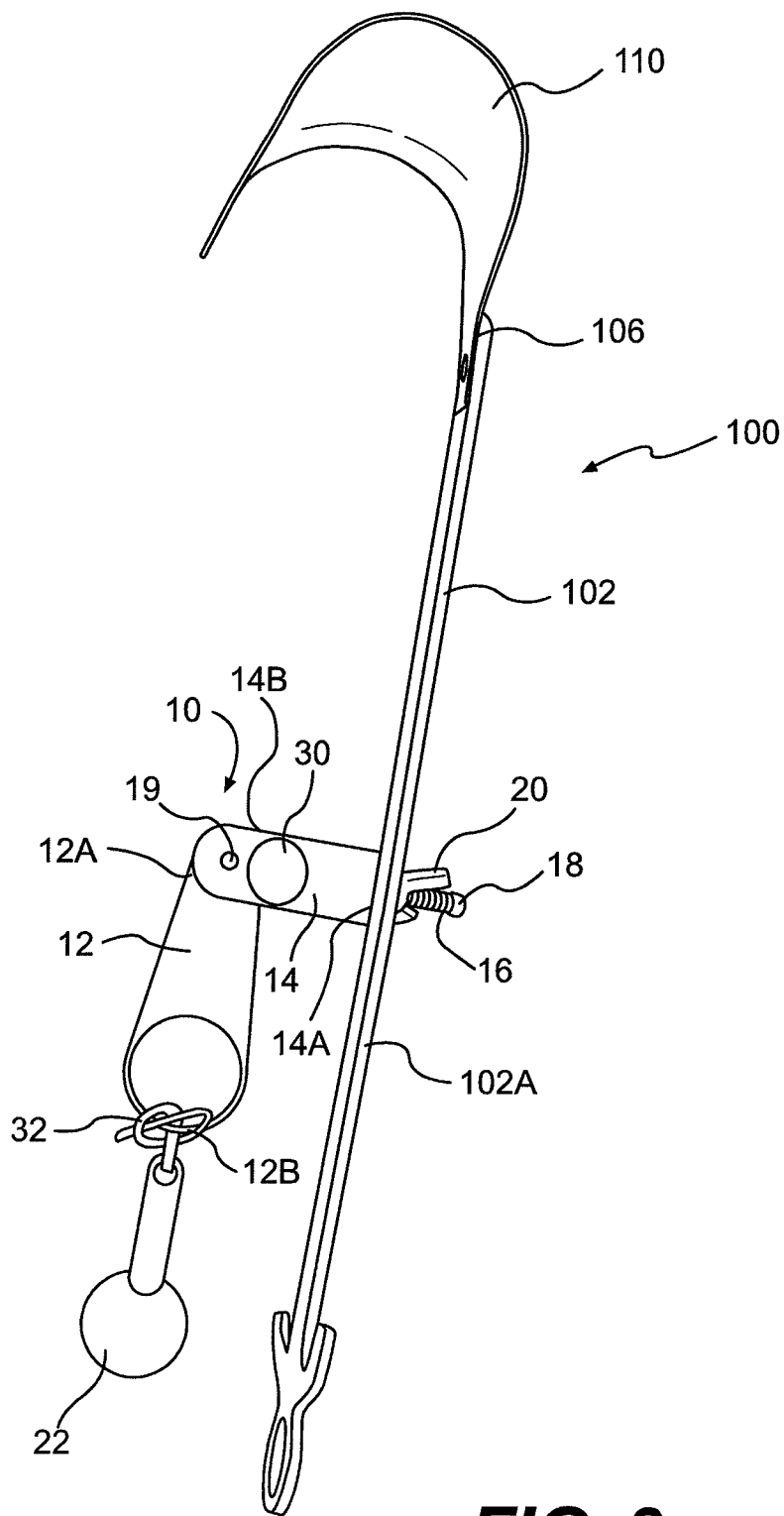
FIG. 3 is a perspective view of a balfour retractor blade with the self retaining adaptor extending substantially parallel to an intermediate portion of the balfour retractor blade.
Figure 4:
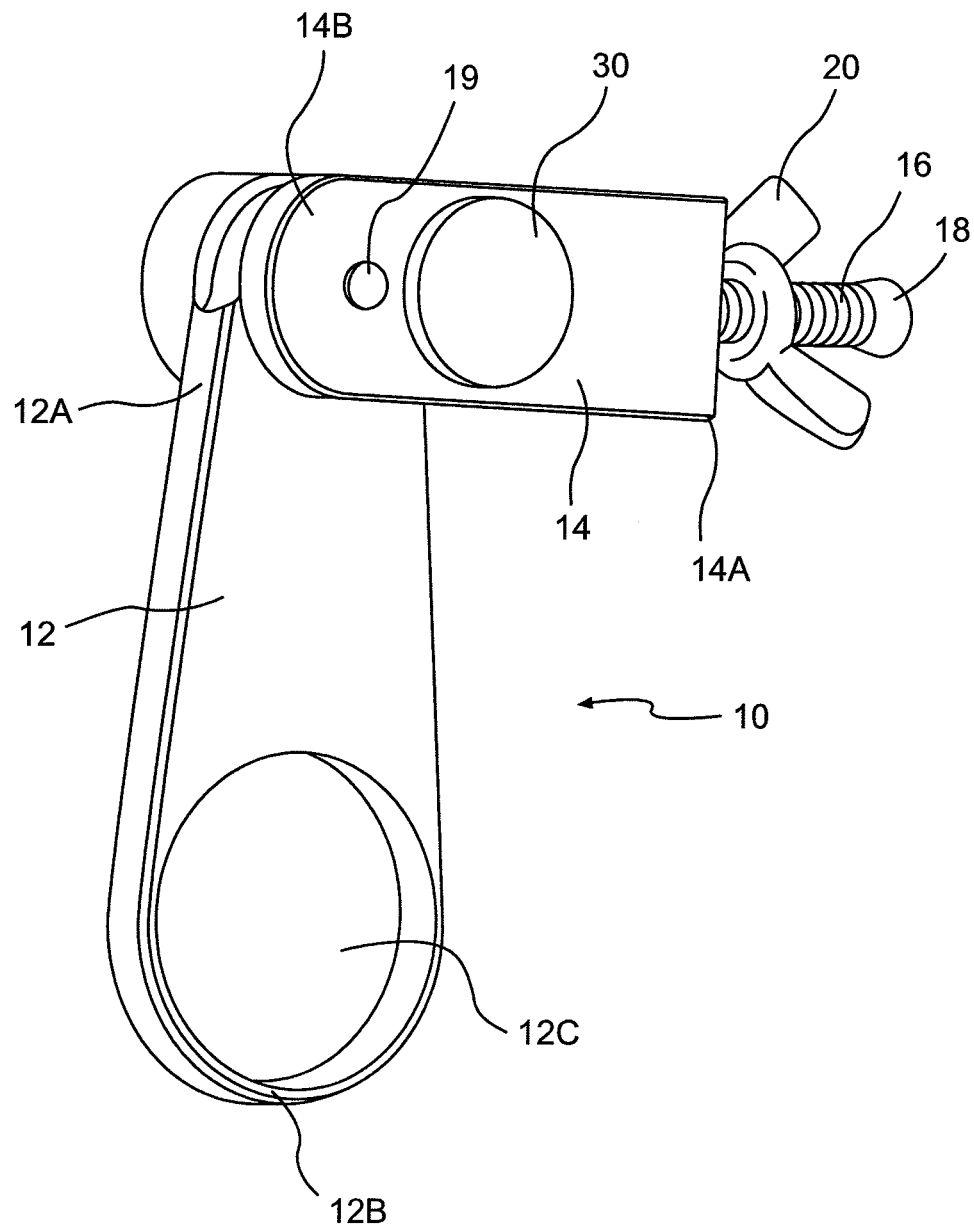
FIG. 4 is an enlarged perspective view of the self retaining adaptor extending substantially orthogonally relative to a secured end of the self retaining adaptor.

As illustrated in FIGS. 1, 2 and 3, a predetermined weight 22 may be attached by means of gauze 32 or any other suitable means to the free end 12 of the self retaining adaptor 10 for enabling hands free use of the balfour retractor blade 100. Depending on the size of the patient and the conditions of the operation, the self retaining adaptor 10 may extend at a plurality of various angles relative to the elongated element 102. For example, as illustrated in FIG. 1, the self retaining adaptor 10 may be positioned substantially orthogonal relative to the elongated element 102. In this position, the weight 22 would pull downwardly on the balfour retractor blade 100.

As illustrated in FIG. 2, the self retaining adaptor 10 may have the free end 12 positioned at substantially a 45 degree angle relative to the secured end 14. In this position, the weight 22 would pull downwardly at a distinct angle of traction for the balfour retractor blade 100.

As illustrated in FIG. 3, the self retaining adaptor 10 may have the free end 12 positioned at substantially a 90 degree angle relative to the secured end 14. In this position, the weight 22 would pull downwardly at a different distinct angle of traction for the balfour retractor blade 100 as compared to the downward force illustrated in FIGS. 1 and 2.

Further, the free end 12 may be rotated upwardly, not illustrated in the drawings, wherein the 45 degree angle and the 90 degree angle illustrated in FIGS. 2 and 3 would be formed on the top side of the secured end 14.

The elongated slot 102B extends from adjacent the proximal end 104 of the elongated element 102 to a predetermined point adjacent to the distal end 106 of the elongated element 102. The elongated slot 102B includes a plurality of enlarged openings 102C for receiving the retaining member 20 through the enlarged portion 102C for enabling a positioning of the self retaining retractor relative to the elongated slot.

The retaining member 20 may be wing nut 20A and the projection 16 may be threaded for enabling the self retaining adaptor 10 to be secured relative to the elongated slot 102B in the elongated element 102 by threading the wing nut 20A on the threaded projection 16 for securing the self retaining adaptor 10 relative to the elongated element 102. The end of the threaded projection 16 may include an enlarged portion 18 for ensuring that the wing nut 20A is not disengaged from the threaded portion 16 during use.

The secured end 14 of the self retaining adaptor 10 includes a proximal end 14A and a distal end 14B. The proximal end 14A includes said projection 16 extending therefrom. The free end 12 includes a proximal end 12A and a distal end 12B. The proximal end 12A of the free end 12 is pivotably mounted at a pivotable connection 19 relative to the distal end 14B of the secured end 14.

A ratchet connection 30 is formed adjacent to the pivotable connection 19 of the proximal end 12A of the free end 12 and the distal end 14B of the secured end 14 for holding the positioning of the free end 12 relative to the secured end 14 in a plurality of angular relationships relative to each other.

The distal end 12B of said free end 12 includes an aperture 12C formed therein for mounting a predetermined weight to enabling the hands free use of the balfour retractor blade.

It is to be understood that because of the variations in the size between individuals and between the pelvic regions of a female during a C-section, various length retractors 100 will normally be required.

In addition to the use of the retractor 100 in a C-section, it is to be understood that the present invention may also be useful in rectosigmoid surgery, in gallbladder surgery and in hysterectomy operations and in the surgical treatment of hiatus hernia conditions.

Figure 5:
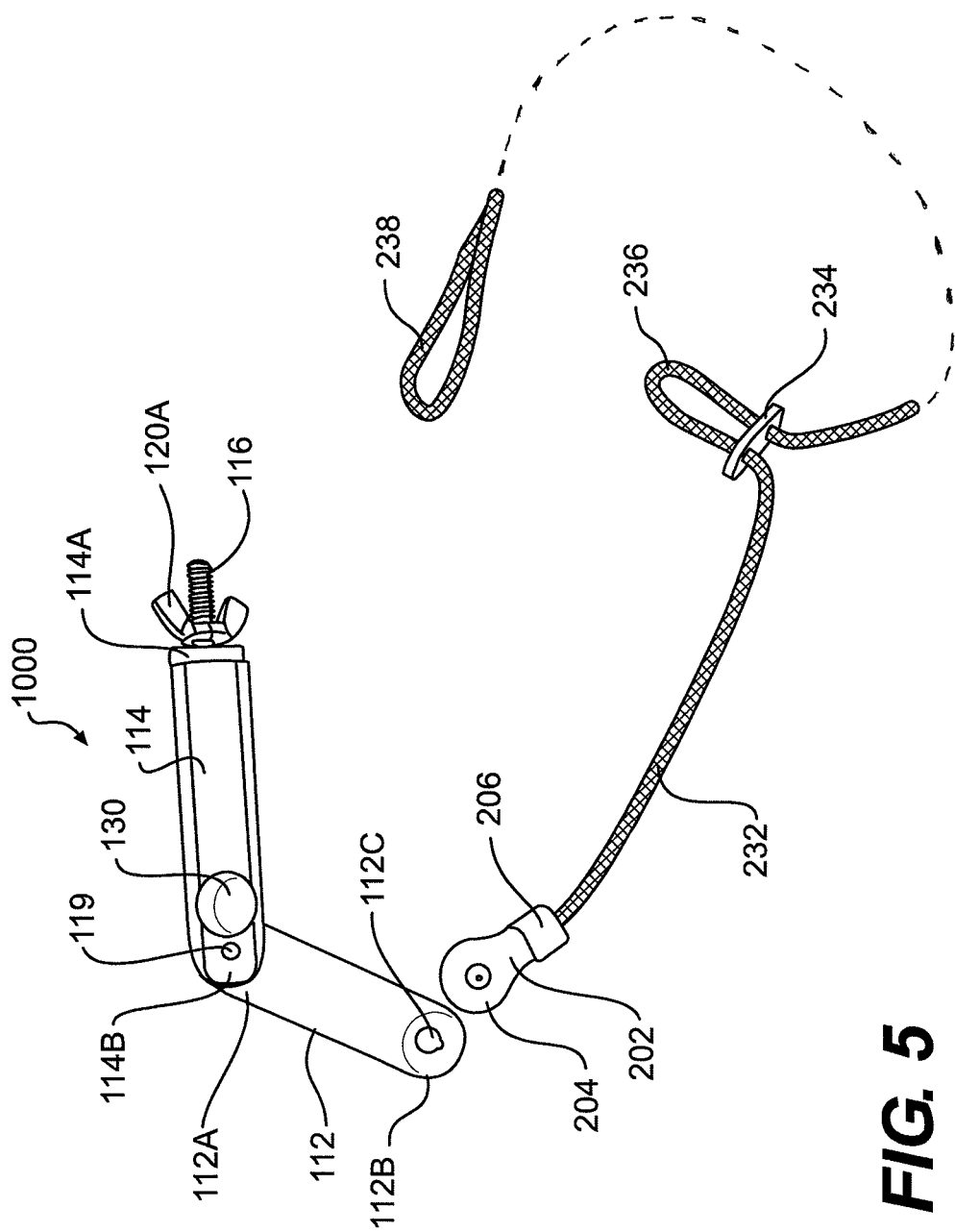
FIG. 5 is an enlarged perspective view of a second embodiment of the self retaining adaptor.

As illustrated in FIG. 5, a second embodiment of the present invention provides a self retaining adaptor 1000 that enables hands free use of a balfour retractor blade.

A self retaining adaptor 1000 includes a free end 112 and a secured end 114. The secured end 114 includes a projection 116 extending therefrom for positioning within the elongated slot 102B in the intermediate portion 102A of the balfour retractor blade 100 illustrated in FIGS. 1 and 2.

A retaining member 120A is operatively attached to the projection 116 for mounting the secured end 114 of the self retaining adaptor 1000 in a fixed position relative to the intermediate portion 102A.

As illustrated in FIG. 5, the secured end 114 of the self retaining adaptor 1000 includes a proximal end 114A and a distal end 114B. The proximal end 114A includes said projection 116 extending therefrom. The free end 112 includes a proximal end 112A and a distal end 112B. The proximal end 112A of the free end 112 is pivotably mounted at a pivotable connection 119 relative to the distal end 114B of the secured end 114.

A ratchet connection 130 is formed adjacent to the pivotable connection 119 of the proximal end 112A of the free end 112 and the distal end 114B of the secured end 114 for holding the positioning of the free end 112 relative to the secured end 114 in a plurality of angular relationships relative to each other.

The distal end 112B of said free end 112 includes an aperture 112C formed therein for mounting an attachment mechanism 202 having a projection 204 for mating with the aperture 112C formed in the distal end 112B of the free end 112. The projection 204 is designed to fit within the aperture 112C for removably securing the attachment mechanism 202 relative to the distal end 112B of the free end 112.

The attachment mechanism 202 includes an end 206 for securing to a cord 232 wherein a weight (not shown) may be attached to a loop 238 formed on a free end of the cord 232. An adjustment member 234 is positioned along the length 236 of the cord 232 for selectively adjusting the length of the cored 232 relative to the distal end 112B of the free end 112 and the predetermined weight for enabling hands free use of the balfour retractor blade.

It is anticipated that the attaching mechanism 202 will be a disposable item for use during a single surgical procedure. The projection 204 may form a snap connection device for snap fitting into the aperture 112C in the distal end 112B of the free end 112.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A device for enabling hands free use of a balfour retractor blade comprising:
   an elongated element having a proximal end and a distal end;
   a curved blade mounted on the distal end of the elongated element, said curved blade projecting substantially orthogonally relative to the elongated element;
   an intermediate portion extending from the proximal end to the distal end, said intermediate portion having a predetermined width with an elongated slot being formed therein;
   a self retaining adaptor having a free end and a secured end, said secured end including a projection extending therefrom for positioning within the elongated slot in the intermediate portion, said self retaining adaptor projecting substantially orthogonally relative to the elongated element and in the same direction as the curved blade; and
   a retaining means operatively attached to the projection for mounting said secured end of the self retaining adaptor in a fixed position relative to the intermediate portion;
   a distal end of the free end of the self retaining adaptor includes an aperture formed therein for securing a predetermined weight for enabling the hands free use of the balfour retractor blade.

2. The device for enabling hands free use of a balfour retractor blade according to claim 1, wherein the elongated slot extends from adjacent the proximal end of the elongated element to a predetermined point adjacent to the distal end of the elongated element, said elongated slot includes at least one enlarged portion for receiving the retaining means through the enlarged portion for enabling a positioning of the self retaining adaptor relative to the elongated slot.

3. The device for enabling hands free use of a balfour retractor blade according to claim 2, wherein the retaining means includes a wing nut and the projection is threaded for enabling the self retaining adaptor to be secured relative to the elongated slot in the elongated element by threading the wing nut on the threaded projection for securing the self retaining adaptor relative to the elongated element.

4. The device for enabling hands free use of a balfour retractor blade according to claim 1, wherein the secured end of the self retaining adaptor includes a proximal end and a distal end, said proximal end includes said projection extending therefrom, said free end includes a proximal end and a distal end, said proximal end of said free end is pivotably mounted relative to the distal end of the secured end.

5. The device for enabling hands free use of a balfour retractor blade according to claim 4, and further including a ratchet connection formed adjacent to the pivotable connection of the proximal end of the free end and the distal end of the secured end for holding the positioning of the free end relative to the secured end in a plurality of angular relationships relative to each other.

6. The device for enabling hands free use of a balfour retractor blade according to claim 4, wherein the distal end of said free end includes an aperture formed therein for mounting a predetermined weight to enabling the hands free use of the balfour retractor blade.

7. The device for enabling hands free use of a balfour retractor blade according to claim 1, wherein the aperture in the distal end of said free end is formed for mating with an attaching mechanism for securing a cord to the attaching member for securing the predetermined weight to the cord for enabling the hands free use of the balfour retractor blade.

8. The device for enabling hands free use of a balfour retractor blade according to claim 7, wherein the attaching mechanism includes a projection extending therefrom for mating with said aperture in the distal end of said free end for releasably securing the attaching mechanism to the distal end of the free end.

9. A device for enabling hands free use of a balfour retractor blade comprising:
   an elongated element having a proximal end and a distal end; an intermediate portion
   extending from the proximal end to the distal end, said intermediate portion having a predetermined width with an elongated slot being formed therein;
   a gripping portion with finger engaging projections formed at the proximal end of the elongated element;
   a retractor being secured to the distal end of the elongated element;
   a self retaining adaptor having a free end and a secured end, said secured end including a projection extending therefrom for positioning within the elongated slot in the intermediate portion; and
   a retainer operatively attached to the projection for mounting said secured end of the self retaining adaptor in a fixed position relative to the intermediate portion;
   wherein the distal end of said free end of the self retaining adaptor includes an aperture formed therein for mating with an attaching mechanism for securing a cord to the distal end of the free end for securing a predetermined weight to the cord for enabling the hands free use of the balfour retractor blade.

10. The device for enabling hands free use of a balfour retractor blade according to claim 9, wherein the elongated slot extends from adjacent the proximal end of the elongated element to a predetermined point adjacent to the distal end of the elongated element, said elongated slot includes at least one enlarged portion for receiving the retainer through the enlarged portion for enabling a positioning of the self retaining adaptor relative to the elongated slot.

11. The device for enabling hands free use of a balfour retractor blade according to claim 10, wherein the retainer includes a wing nut and the projection is threaded for enabling the self retaining adaptor to be secured relative to the elongated slot in the elongated element by threading the wing nut on the threaded projection for securing the self retaining adaptor relative to the elongated element.

12. The device for enabling hands free use of a balfour retractor blade according to claim 9, wherein the secured end of the self retaining adaptor includes a proximal end and a distal end, said proximal end includes said projection extending therefrom, said free end includes a proximal end and a distal end, said proximal end of said free end is pivotably mounted relative to the distal end of the secured end.

13. The device for enabling hands free use of a balfour retractor blade according to claim 12, and further including a ratchet connection formed adjacent to the pivotable connection of the proximal end of the free end and the distal end of the secured end for holding the positioning of the free end relative to the secured end in a plurality of angular relationships relative to each other.

14. The device for enabling hands free use of a balfour retractor blade according to claim 12, wherein the distal end of said free end includes an aperture formed therein for mounting a predetermined weight to enabling the hands free use of the balfour retractor blade.

15. The device for enabling hands free use of a balfour retractor blade according to claim 9, wherein the attaching mechanism includes a projection extending therefrom for mating with said aperture in the distal end of said free end for releasably securing the attaching mechanism to the distal end of the free end.

16. A device for enabling hands free use of a balfour retractor blade comprising:
   an elongated element having a proximal end and a distal end;
   an intermediate portion extending from the proximal end to the distal end, said intermediate portion having a predetermined width with an elongated slot being formed therein;
   a self retaining adaptor having a free end and a secured end, said secured end including a projection extending therefrom for positioning within the elongated slot in the intermediate portion; and
   a retaining means operatively attached to the projection for mounting said secured end of the self retaining adaptor in a fixed position relative to the intermediate portion; and
   a distal end of the free end of the self retaining adaptor includes an aperture formed therein for mating with an attaching mechanism for securing a cord to the distal end of the free end for securing a predetermined weight to the cord for enabling the hands free use of the balfour retractor blade.

17. The device for enabling hands free use of a balfour retractor blade according to claim 16, wherein the elongated slot extends from adjacent the proximal end of the elongated element to a predetermined point adjacent to the distal end of the elongated element, said elongated slot includes at least one enlarged portion for receiving the retaining means through the enlarged portion for enabling a positioning of the self retaining adaptor relative to the elongated slot.

18. The device for enabling hands free use of a balfour retractor blade according to claim 17, wherein the retaining means includes a wing nut and the projection is threaded for enabling the self retaining adaptor to be secured relative to the elongated slot in the elongated element by threading the wing nut on the threaded projection for securing the self retaining adaptor relative to the elongated element.

19. The device for enabling hands free use of a balfour retractor blade according to claim 16, wherein the secured end of the self retaining adaptor includes a proximal end and a distal end, said proximal end includes said projection extending therefrom, said free end includes a proximal end and a distal end, said proximal end of said free end is pivotably mounted relative to the distal end of the secured end.

20. The device for enabling hands free use of a balfour retractor blade according to claim 19, and further including a ratchet connection formed adjacent to the pivotable connection of the proximal end of the free end and the distal end of the secured end for holding the positioning of the free end relative to the secured end in a plurality of angular relationships relative to each other.

* * * * *